(12) United States Patent
Raphy et al.

(10) Patent No.: US 8,957,090 B2
(45) Date of Patent: Feb. 17, 2015

(54) FUSED BICYCLIC PYRIDINE AND PYRAZINE DERIVATIVES AS KINASE INHIBITORS

(75) Inventors: Gilles Raphy, Saffron Walden Essex (GB); Roland Bürli, Saffron Walden Essex (GB); Alan Findlay Haughan, Saffron Walden Essex (GB)

(73) Assignee: UCB Pharma S.A., Brussels (BE)

( * ) Notice: Subject to any disclaimer, the term of this patent is extended or adjusted under 35 U.S.C. 154(b) by 348 days.

(21) Appl. No.: 13/508,964

(22) PCT Filed: Nov. 11, 2010

(86) PCT No.: PCT/EP2010/067310
§ 371 (c)(1),
(2), (4) Date: Sep. 24, 2012

(87) PCT Pub. No.: WO2011/058113
PCT Pub. Date: May 19, 2011

(65) Prior Publication Data
US 2013/0012515 A1    Jan. 10, 2013

(30) Foreign Application Priority Data

Nov. 12, 2009 (GB) .................................. 0919819.3
Jun. 23, 2010 (GB) .................................. 1010583.1

(51) Int. Cl.
*A61K 31/47* (2006.01)
*C07D 215/00* (2006.01)
*C07D 401/12* (2006.01)
*C07D 473/02* (2006.01)
*C07D 487/04* (2006.01)

(52) U.S. Cl.
CPC ............ *C07D 401/12* (2013.01); *C07D 473/02* (2013.01); *C07D 487/04* (2013.01)
USPC ........................................... 514/312; 546/157

(58) Field of Classification Search
CPC ... C07D 401/12; C07D 473/02; C07D 487/04
USPC ........................................... 514/312; 546/157
See application file for complete search history.

(56) References Cited

FOREIGN PATENT DOCUMENTS

| FR | 2 532 939 A1 | 3/1984 |
| WO | 2006/131519 A1 | 12/2006 |
| WO | 2007/075946 A1 | 7/2007 |
| WO | 2009/081105 A2 | 7/2009 |

OTHER PUBLICATIONS

Vogel, M et al., "Quinoxalines. XXIV. Synthesis of 4-Substituted 1,2,3-Triazolo [1, 5-a] quinoxalines", Journal Fur Praktische Chemie, 1987, 329(1), 101-107.

*Primary Examiner* — Sreeni Padmanabhan
*Assistant Examiner* — Jody Karol
(74) *Attorney, Agent, or Firm* — McDonnell Boehnen Hulbert & Berghoff LLP

(57) ABSTRACT

A series of fused bicyclic pyridine and pyrazine derivatives, substituted directly on the pyridine or pyrazine ring by a functional group attached via a sulphur-containing linkage, being selective inhibitors of P13 kinase enzymes, are accordingly of benefit in medicine, for example in the treatment of inflammatory, autoimmune, cardiovascular, neurodegenerative, metabolic, oncological, nociceptive or ophthalmic conditions.

9 Claims, No Drawings

FUSED BICYCLIC PYRIDINE AND PYRAZINE DERIVATIVES AS KINASE INHIBITORS

This application is a US national phase of International Application No. PCT/EP2010/067310 filed on Nov. 11, 2010, the disclosure of which is incorporated herein by reference in its entirety.

The present invention relates to a class of fused bicyclic pyridine and pyrazine derivatives, and to their use in therapy. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

WO 2008/118454, WO 2008/118455 and WO 2008/118468 describe various series of quinoline and quinoxaline derivatives that are structurally related to each other and are stated to be useful to inhibit the biological activity of human PI3Kδ and to be of use in treating PI3K-mediated conditions or disorders.

WO 2009/081105, copending international application PCT/GB2009/002504, published on 29 Apr. 2010 as WO 2010/046639 (claiming priority from United Kingdom patent application 0819593.5), copending international application PCT/GB2010/000243, published on 19 Aug. 2010 as WO 2010/092340 (claiming priority from United Kingdom patent applications 0902450.6 and 0914533.5), copending international application PCT/GB2010/000361, published on 10 Sep. 2010 as WO 2010/100405 (claiming priority from United Kingdom patent applications 0903949.6 and 0915586.2), and copending international application PCT/GB2010/001000 (claiming priority from United Kingdom patent application 0908957.4) describe separate classes of fused bicyclic heteroaryl derivatives as selective inhibitors of PI3K enzymes that are of benefit in the treatment of adverse inflammatory, autoimmune, cardiovascular, neurodegenerative, metabolic, oncological, nociceptive and ophthalmic conditions.

Copending international patent application PCT/US2009/005380, published on 1 Apr. 2010 as WO 2010/036380, describes a family of pyridine and pyrazine derivatives that are stated to be selective inhibitors of type I PI3 kinases and to be of use in treating a medical condition mediated by a type I PI3 kinase.

None of the prior art available to date, however, discloses or suggests the precise structural class of fused bicyclic pyridine and pyrazine derivatives as provided by the present invention. In particular, none of the available prior art publications specifically exemplifies substitution by a sulphur-containing functional group directly on the pyridine or pyrazine ring.

The compounds of the present invention are potent and selective PI3K inhibitors having a binding affinity ($IC_{50}$) for the human PI3Kα and/or PI3Kβ and/or PI3Kγ and/or PI3Kδ isoform of 50 µM or less, generally of 20 µM or less, usually of 5 µM or less, typically of 1 µM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides a compound of formula (I) or an N-oxide thereof, or a pharmaceutically acceptable salt or solvate thereof:

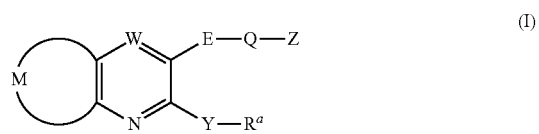

wherein

M represents the residue of an optionally substituted phenyl ring; or an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl and triazolyl; or an optionally substituted six-membered heteroaromatic ring selected from pyridinyl, pyridazinyl, pyrimidinyl, pyrazinyl and triazinyl;

W represents C—$R^1$ or N;

E represents an optionally substituted straight or branched $C_{1-4}$ alkylene chain;

Q represents oxygen, sulfur, N—$R^2$ or a covalent bond;

Z represents an optionally substituted mono- or bicyclic heteroaryl group containing at least one nitrogen atom;

Y represents —S—, —S(O)— or —S(O)$_2$—;

R[1] represents hydrogen, halogen, C$_{1-6}$ alkyl or C$_{1-6}$ alkoxy;

R[2] represents hydrogen or C$_{1-6}$ alkyl; and

R$^a$ represents trifluoromethyl; or C$_{1-6}$ alkyl, C$_{2-6}$ alkenyl, C$_{3-7}$ cycloalkyl, C$_{3-7}$ cycloalkyl(C$_{1-6}$)alkyl, aryl, aryl(C$_{1-6}$)alkyl, C$_{3-7}$ heterocycloalkyl, C$_{3-7}$ heterocycloalkyl-(C$_{1-6}$)alkyl, heteroaryl or heteroaryl(C$_{1-6}$)alkyl, any of which groups may be optionally substituted by one or more substituents.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched C$_{1-6}$ alkyl groups, for example C$_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "C$_{1-6}$ alkoxy", "C$_{1-6}$ alkylthio", "C$_{1-6}$ alkylsulphonyl" and "C$_{1-6}$ alkylamino" are to be construed accordingly.

The expression "C$_{1-3}$ alkylene chain" refers to a divalent straight or branched alkylene chain containing 1 to 3 carbon atoms. Typical examples include methylene, ethylene, methylmethylene, ethylmethylene and dimethylmethylene.

Specific C$_{3-7}$ cycloalkyl groups are cyclopropyl, cyclobutyl, cyclopentyl, cyclohexyl and cycloheptyl.

Suitable aryl groups include phenyl and naphthyl, preferably phenyl.

Suitable aryl(C$_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydro-quinoxalinyl, homopiperazinyl, morpholinyl, benzoxazinyl and thiomorpholinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, pyrazolo[3,4-d]pyrimidinyl, indazolyl, oxazolyl, benzoxazolyl, isoxazolyl, thiazolyl, benzothiazolyl, isothiazolyl, imidazolyl, benzimidazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH$_2$C=O)$\leftrightarrow$ enol (CH=CHOH) tautomers or amide (NHC=O)$\leftrightarrow$ hydroxyimine (N=COH) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1$H, $^2$H (deuterium) or $^3$H (tritium) atom, preferably $^1$H. Similarly, by way of example, each individual carbon atom present in formula (I), or in the formulae depicted hereinafter, may be present as a $^{12}$C, $^{13}$C or $^{14}$C atom, preferably $^{12}$C.

In one embodiment, W represents C—R[1]. In another embodiment, W represents N.

Specific sub-classes of compounds in accordance with the present invention are represented by the compounds of formula (IA) and (IB), especially (IA):

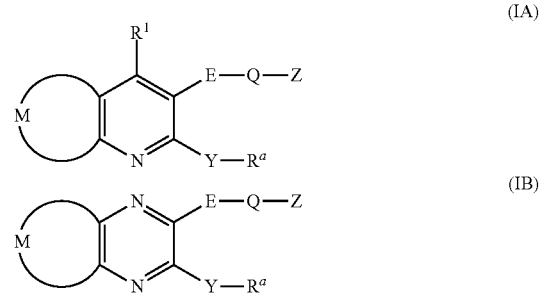

wherein M, E, Q, Z, Y, R[1] and R$^a$ are as defined above.

In the compounds of formula (I), the moiety M is defined as representing the residue of an optionally substituted phenyl ring, or of an optionally substituted five-membered or six-membered heteroaromatic ring as specified above. From this it is to be understood that the variable M, when taken together with the two carbon atoms of the pyridine or pyrazine ring to which the M-containing ring is fused, represents an optionally substituted phenyl ring, or an optionally substituted five-membered or six-membered heteroaromatic ring as specified above.

In one embodiment, the moiety M in the compounds of formula (I) above represents the residue of an optionally substituted phenyl ring. In another embodiment, the moiety M in the compounds of formula (I) above represents the residue of an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl, triazolyl and tetrazolyl. In a further embodiment, the moiety M in the compounds of formula (I) above represents the residue of an optionally substituted six-membered heteroaromatic ring selected from pyridinyl, pyridazinyl, pyrimidinyl, pyrazinyl and triazinyl.

Suitably, the moiety M represents the residue of a phenyl ring, which may be optionally substituted by one or two substituents. In one embodiment, the moiety M represents the residue of a monosubstituted phenyl ring. In another embodiment, the moiety M represents the residue of a disubstituted phenyl ring.

The ring of which the moiety M is the residue may be unsubstituted, or may suitably be substituted, where possible, by one more, typically by one or two, substituents. In one embodiment, this ring is unsubstituted. In another embodiment, this ring is monosubstituted. In a further embodiment, this ring is disubstituted. Examples of typical substituents on the ring of which the moiety M is the residue include $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl, heteroaryl($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$)alkylamino, halogen, cyano and trifluoromethyl.

Typically, the ring of which the moiety M is the residue may optionally be substituted by one or more substituents selected from $C_{1-6}$ alkyl and halogen.

Suitably, the ring of which the moiety M is the residue may optionally be substituted by $C_{1-6}$ alkyl, especially methyl.

Suitably, the ring of which the moiety M is the residue may optionally be substituted by halogen, especially fluoro or chloro. In one embodiment, the ring of which the moiety M is the residue is optionally substituted by fluoro. In another embodiment, the ring of which the moiety M is the residue is optionally substituted by chloro.

Typical values of E include methylene (—$CH_2$—), (methyl)methylene, ethylene (—$CH_2CH_2$—), (ethyl)methylene, (dimethyl)methylene, (methyl)ethylene, (propyl)methylene and (dimethyl)ethylene, any of which chains may be optionally substituted by one or more substituents. Suitably, such chains are unsubstituted, monosubstituted or disubstituted. Preferably, such chains are unsubstituted or monosubstituted. In one embodiment, such chains are unsubstituted. In another embodiment, such chains are monosubstituted.

Examples of suitable substituents on the alkylene chain represented by E include trifluoromethyl, $C_{3-7}$ heterocycloalkyl, aryl, oxo, hydroxy, $C_{1-6}$ alkoxy, $C_{2-6}$ alkoxy-carbonyl($C_{1-6}$)alkoxy, aminocarbonyl($C_{1-6}$)alkoxy, trifluoromethoxy, amino, $C_{1-6}$ alkylamino, di($C_{1-6}$)alkylamino, aminocarbonyl, $C_{1-6}$ alkylaminocarbonyl and di($C_{1-6}$)alkylaminocarbonyl.

Examples of particular substituents on the alkylene chain represented by E include trifluoromethyl, pyrrolidinyl, piperidinyl, piperazinyl, morpholinyl, phenyl, oxo, hydroxy, ethoxy, ethoxycarbonylmethoxy, aminocarbonylmethoxy, trifluoromethoxy, amino, methylamino, dimethylamino, aminocarbonyl, methylaminocarbonyl and dimethylamino-carbonyl.

Suitable values of E include methylene (—$CH_2$—) and (methyl)methylene.

A particular value of E is (methyl)methylene, i.e. —CH($CH_3$)—.

Another value of E is methylene, i.e. —$CH_2$—.

Suitable values of Q include oxygen and N—$R^2$.

In one embodiment, Q represents oxygen. In another embodiment, Q represents sulfur. In a further embodiment, Q represents N—$R^2$. In a still further embodiment, Q represents a covalent bond.

The expression "mono- or bicyclic heteroaryl group containing at least one nitrogen atom" in relation to the group Z refers in particular to a mono- or bicyclic aromatic ring system containing one, two, three or four heteroatoms selected from oxygen, sulfur and nitrogen atoms, with at least one of the heteroatoms being nitrogen. The ring Z may be linked to the group Q (or E, where Q represents a covalent bond) through any available carbon or nitrogen atom.

In one embodiment, Z is monocyclic. In another embodiment, Z is bicyclic. In one aspect of that embodiment, the bicyclic heteroaryl group Z comprises two fused six-membered rings. In another aspect of that embodiment, the bicyclic heteroaryl group Z comprises a furan, thiophene, oxazole, thiazole, isoxazole or isothiazole ring fused to a five-membered or six-membered ring.

Suitable examples of Z include pyrrolyl, pyridinyl, quinolinyl, isoquinolinyl, imidazolyl, pyrazolyl, triazolyl, pyridazinyl, pyrimidinyl, pyrazinyl, triazinyl, indazolyl, benzimidazolyl, furopyridinyl, thienopyridinyl, benzoxazolyl, benzothiazolyl, cinnolinyl, phthalazinyl, quinazolinyl, quinoxalinyl, imidazopyridinyl, pyrazolopyridinyl, purinyl, pyrazolopyrimidinyl, pyrrolopyrimidinyl, triazolopyrimidinyl, pyridopyrimidinyl, pyridopyrazinyl, pyridopyridazinyl, naphthyridinyl, pteridinyl, pyrrolotriazinyl and pyrazolotriazinyl, any of which groups may be optionally substituted by one or more substituents.

Illustrative examples of Z include pyrrolyl, pyridinyl, quinolinyl, isoquinolinyl, imidazolyl, pyrazolyl, triazolyl, pyridazinyl, pyrimidinyl, pyrazinyl, triazinyl, furopyridinyl, thienopyridinyl, benzoxazolyl, benzothiazolyl, cinnolinyl, phthalazinyl, quinazolinyl, quinoxalinyl, pyridopyrimidinyl, pyridopyrazinyl, pyridopyridazinyl, naphthyridinyl and pteridinyl, any of which groups may be optionally substituted by one or more substituents.

Typically, Z may represent pyrrolyl, pyridin-2-yl, pyridin-3-yl, indolyl, isoquinolinyl, imidazolyl, pyrazolyl, triazolyl, pyridazinyl, pyrimidin-2-yl, pyrimidin-5-yl, pyrazinyl, triazinyl, indazolyl, furopyridinyl, thienopyridinyl, benzoxazolyl, benzothiazolyl, cinnolinyl, phthalazinyl, quinazolinyl, purin-1-yl, purin-2-yl, purin-3-yl, 7H-purin-6-yl, 9H-purin-6-yl, purin-7-yl, purin-8-yl, pyrazolo[3,4-d]pyrimidin-4-yl, triazolopyrimidinyl, pyridopyrimidin-4-yl, pyridopyrazinyl, pyridopyridazinyl, naphthyridinyl, pteridinyl, pyrrolotriazinyl or pyrazolotriazinyl, any of which groups may be optionally substituted by one or more substituents. Additionally, Z may represent optionally substituted pyrimidin-4-yl.

Selected values of Z include pyrimidinyl (especially pyrimidin-2-yl or pyrimidin-4-yl), triazinyl, purinyl (especially 9H-purin-6-yl) and pyrrolotriazinyl (especially pyrrolo[2,1-f][1,2,4]triazin-4-yl), any of which groups may be optionally substituted by one or more substituents.

Typical values of Z include triazinyl and pyrrolotriazinyl (especially pyrrolo[2,1-f][1,2,4]triazin-4-yl), either of which groups may be optionally substituted by one or more substituents.

Examples of optional substituents which may be present on the group Z include one, two or three substituents independently selected from halogen, cyano, nitro, oxo, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Illustrative examples of optional substituents on the group Z include halogen, cyano, $C_{1-6}$ alkyl and amino.

Selected examples of optional substituents on the group Z include cyano, $C_{1-6}$ alkyl and amino.

Typical examples of optional substituents on the group Z include $C_{1-6}$ alkyl and amino.

Examples of particular substituents on the group Z include fluoro, chloro, bromo, cyano, nitro, oxo, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methoxycarbonylamino, methylsulfonylamino, formyl, acetyl, cyclopropylcarbonyl, azetidinylcarbonyl, N-methylazetidinylcarbonyl, pyrrolidinylcarbonyl, N-methylpyrrolidinylcarbonyl, piperidinylcarbonyl, N-methylpiperidinylcarbonyl, piperazinylcarbonyl, N-methylpiperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Illustrative examples of particular substituents on the group Z include chloro, cyano, methyl and amino.

Selected examples of particular substituents on the group Z include cyano, methyl and amino.

Typical examples of particular substituents on the group Z include methyl and amino.

In one embodiment, Z represents optionally substituted triazinyl. In one aspect of that embodiment, Z represents 4-amino-6-methyl-[1,3,5]triazin-2-yl.

In another embodiment, Z represents optionally substituted pyrrolotriazinyl. In one aspect of that embodiment, Z represents pyrrolo[2,1-f][1,2,4]triazin-4-yl.

In another embodiment, Z represents optionally substituted pyrimidinyl. In one aspect of that embodiment, Z represents optionally substituted pyrimidin-2-yl, for example 4-amino-5-cyanopyrimidin-2-yl. In another aspect of that embodiment, Z represents optionally substituted pyrimidin-4-yl, for example 2-amino-5-cyanopyrimidin-4-yl.

In a further embodiment, Z represents optionally substituted purinyl. In one aspect of that embodiment, Z represents 9H-purin-6-yl.

In one embodiment, Y represents —S—. In another embodiment, Y represents —S(O)—. In a further embodiment, Y represents —S(O)$_2$—.

Typically, $R^1$ represents hydrogen or $C_{1-6}$ alkyl.

In one embodiment, $R^1$ represents hydrogen. In another embodiment, $R^1$ represents halogen, particularly fluoro or chloro. In one aspect of that embodiment, $R^1$ represents fluoro. In another aspect of that embodiment, $R^1$ represents chloro. In a further embodiment, $R^1$ represents $C_{1-6}$ alkyl, especially methyl. In an additional embodiment, $R^1$ represents $C_{1-6}$ alkoxy, especially methoxy.

Suitable values of the group $R^1$ include hydrogen, fluoro, chloro, bromo, methyl and methoxy. Suitably, $R^1$ represents hydrogen or methyl. Typically, $R^1$ represents hydrogen.

In one embodiment, $R^2$ represents hydrogen. In another embodiment, $R^2$ represents $C_{1-6}$ alkyl, especially methyl.

Suitable values of the group $R^2$ include hydrogen and methyl.

Generally, $R^a$ may represent trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl-($C_{1-6}$) alkyl, heteroaryl or heteroaryl($C_{1-6}$)alkyl, any of which groups may be optionally substituted by one or more substituents.

Typically, $R^a$ represents optionally substituted $C_{1-6}$ alkyl.

Illustratively, $R^a$ represents trifluoromethyl; or methyl, ethyl, n-propyl, isopropyl, n-butyl, 2-methylpropyl, tert-butyl, pentyl, hexyl, allyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Selected examples of particular values of $R^a$ include methyl, ethyl, n-propyl and isopropyl, any of which groups may be optionally substituted by one or more substituents.

Appositely, $R^a$ represents optionally substituted methyl.

Typical examples of suitable substituents on $R^a$ include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, amino, $C_{1-6}$ alkylamino, di($C_{1-6}$)-alkylamino, phenylamino, pyridinylamino, $C_{2-6}$ alkylcarbonylamino, $C_{2-6}$ alkoxycarbonyl-amino, aminocarbonyl, ($C_{1-6}$) alkylaminocarbonyl and di($C_{1-6}$)alkylaminocarbonyl.

Selected examples of suitable substituents on $R^a$ include hydroxy, aminocarbonyl and ($C_{1-6}$)alkylaminocarbonyl.

Typical examples of specific substituents on $R^a$ include fluoro, chloro, bromo, methyl, ethyl, isopropyl, methoxy, ethoxy, isopropoxy, difluoromethoxy, trifluoromethoxy, methoxymethyl, methylthio, ethylthio, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, amino, methylamino, ethylamino, dimethylamino, phenylamino, pyridinylamino, acetylamino, tert-butoxycarbonylamino, aminocarbonyl, methylaminocarbonyl and dimethylaminocarbonyl.

Particular examples of specific substituents on $R^a$ include hydroxy, aminocarbonyl and methylaminocarbonyl.

A selected example of a specific substituent on $R^a$ is aminocarbonyl.

Selected values of $R^a$ include aminocarbonylmethyl, methylaminocarbonylmethyl, hydroxyethyl, dihydroxypropyl and isopropyl.

A particular value of $R^a$ is aminocarbonylmethyl.

One sub-class of compounds according to the invention is represented by the compounds of formula (IIA) and N-oxides thereof, and pharmaceutically acceptable salts and solvates thereof:

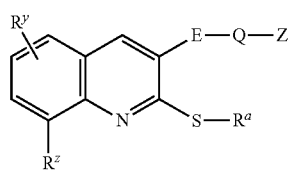

(IIA)

wherein E, Q, Z and $R^a$ are as defined above; and $R^y$ and $R^z$ independently represent hydrogen, $C_{1-6}$ alkyl, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl($C_{1-6}$) alkyl, heteroaryl, heteroaryl($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$) alkylamino, halogen, cyano or trifluoromethyl.

Typically, $R^y$ represents hydrogen or halogen. Suitably, $R^y$ represents hydrogen.

In one embodiment, $R^y$ represents hydrogen. In another embodiment, $R^y$ represents halogen. In one aspect of that embodiment, $R^y$ represents fluoro. In another aspect of that embodiment, $R^y$ represents chloro.

Typically, $R^z$ represents hydrogen, $C_{1-6}$ alkyl or halogen. Appositely, $R^z$ represents $C_{1-6}$ alkyl or halogen. Suitably, $R^z$ represents $C_{1-6}$ alkyl, especially methyl.

In one embodiment, $R^z$ represents hydrogen. In another embodiment, $R^z$ represents $C_{1-6}$ alkyl. In one aspect of that embodiment, $R^z$ represents methyl. In another aspect of that embodiment, $R^z$ represents ethyl. In a further embodiment, $R^z$ represents halogen. In one aspect of that embodiment, $R^z$ represents fluoro. In another aspect of that embodiment, $R^z$ represents chloro.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above wherein Q represents oxygen, sulfur or N—$R^2$ may be prepared by a process which comprises reacting a compound of formula (III) with a compound of formula (IV):

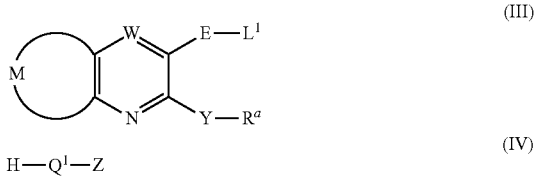

wherein $Q^1$ represents oxygen, sulfur or N—$R^2$, $L^1$ represents a suitable leaving group, and M, W, E, Z, Y, $R^2$ and $R^a$ are as defined above.

The leaving group $L^1$ is typically a halogen atom, e.g. bromo or iodo.

The reaction is conveniently effected at ambient or elevated temperature in a suitable solvent, e.g. N,N-dimethylformamide or acetonitrile. The reaction may be performed in the presence of a suitable base, e.g. an inorganic base such as potassium carbonate, cesium carbonate, sodium hydride or aqueous sodium hydroxide.

The intermediates of formula (III) above wherein $L^1$ is bromo or iodo may be prepared from a compound of formula (V):

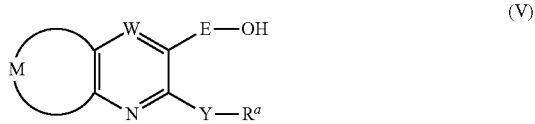

wherein M, W, E, Y and $R^a$ are as defined above; by bromination or iodination.

The bromination reaction is conveniently effected by stirring compound (V) with an appropriate brominating agent, e.g. phosphorus tribromide, in a suitable solvent, e.g. a halogenated hydrocarbon such as dichloromethane.

The iodination reaction is conveniently effected by stirring compound (V) with an appropriate iodinating agent, e.g. elemental iodine, in a suitable solvent, e.g. a halogenated hydrocarbon such as dichloromethane, typically in the presence of triphenylphosphine and imidazole.

Alternatively, the intermediates of formula (III) above wherein E represents methylene and $L^1$ is bromo may be prepared from a compound of formula (VI):

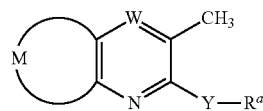

wherein M, W, Y and $R^a$ are as defined above; by bromination.

The reaction is conveniently effected at an elevated temperature in a suitable solvent, e.g. a halogenated solvent such as carbon tetrachloride, in the presence of a suitable brominating agent, e.g. N-bromosuccinimide, typically in the presence of a catalyst such as benzoyl peroxide.

In another procedure, the compounds of formula (I) wherein Q represents oxygen may be prepared by a process which comprises reacting a compound of formula (V) as defined above with a compound of formula (VII):

$$L^2\text{-}Z \qquad \text{(VII)}$$

wherein Z is as defined above, and $L^2$ represents a suitable leaving group.

The leaving group $L^2$ is typically a halogen atom, e.g. chloro or bromo.

The reaction is conveniently effected by stirring compounds (V) and (VII) at an elevated temperature in a suitable solvent, e.g. N,N-dimethylformamide or 1,4-dioxane, typically under basic conditions, e.g. in the presence of an inorganic base such as sodium hydride.

In another procedure, the compounds of formula (I) wherein Q represents sulfur may be prepared by a process which comprises reacting a compound of formula (VII) as defined above with a compound of formula (VIII):

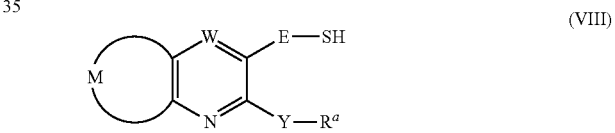

wherein M, W, E, Y and $R^a$ are as defined above.

The reaction is conveniently effected by stirring compounds (VII) and (VIII) in a suitable solvent, e.g. a lower alkanol such as methanol, typically under basic conditions, e.g. in the presence of an alkali metal alkoxide such as sodium methoxide.

The intermediates of formula (VIII) may typically be prepared by treating a suitable compound of formula (III) above with thiolacetic acid; followed by treatment of the resulting compound with a base, e.g. an alkali metal alkoxide such as sodium methoxide.

In another procedure, the compounds of formula (I) wherein Q represents N—$R^2$ may be prepared by a process which comprises reacting a compound of formula (VII) as defined above with a compound of formula (IX):

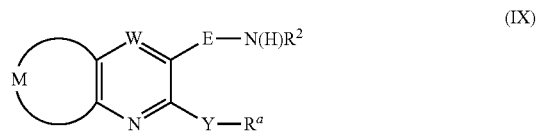

wherein M, W, E, Y, $R^2$ and $R^a$ are as defined above.

The reaction is conveniently effected at an appropriate temperature, e.g. at ambient temperature or at an elevated temperature, in a suitable solvent, e.g. isopropanol, n-butanol, tetrahydrofuran, 1-methyl-2-pyrrolidinone (NMP) or 1,4-dioxane. The reaction may be performed in the presence of a suitable base, e.g. an organic base such as N,N-diisopropylethylamine.

The intermediates of formula (IX) wherein $R^2$ represents hydrogen may be prepared by treating a suitable compound of formula (III) above with potassium phthalimide; followed by treatment of the resulting compound with hydrazine. Alternatively, they may be prepared by treating a suitable compound of formula (III) above with sodium azide; followed by treatment of the resulting compound with triphenylphosphine.

In an additional procedure, the compounds of formula (I) wherein E represents methylene and Q represents N—$R^2$ may be prepared by a process which comprises reacting a compound of formula (IV) above wherein $Q^1$ represents N—$R^2$ with a compound of formula (X):

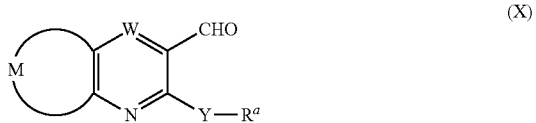

(X)

wherein M, W, Y and $R^a$ are as defined above; under reducing conditions.

The reaction is conveniently effected by stirring the reactants at an elevated temperature in a suitable solvent, e.g. a cyclic ether such as tetrahydrofuran, in the presence of a reducing agent. A suitable reducing agent comprises a mixture of di-n-butyltin dichloride and phenylsilane.

The intermediates of formula (IX) wherein E represents methylene and $R^2$ represents $C_{1-6}$ alkyl, e.g. methyl, may be prepared by treating a suitable compound of formula (X) above with a $C_{1-6}$ alkylamine, e.g. methylamine, in the presence of titanium(IV) n-propoxide and a base, e.g. an organic base such as N,N-diisopropylamine; followed by treatment of the resulting compound with a reducing agent, e.g. sodium triacetoxyborohydride.

The intermediates of formula (V) wherein E represents methylene may be prepared from the corresponding compound of formula (X) by treatment with a reducing agent, e.g. sodium borohydride.

The intermediates of formula (V), (VIII) and (IX) wherein Y represents —S— may be prepared by reacting a compound of formula (XI) with a compound of formula (XII):

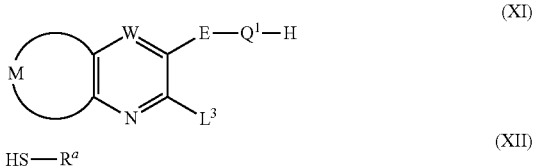

(XI)

(XII)

wherein M, W, E, $Q^1$ and $R^a$ are as defined above, and $L^3$ represents a suitable leaving group.

The leaving group $L^3$ is typically a halogen atom, e.g. chloro.

The reaction is conveniently effected at an elevated temperature in a suitable solvent, e.g. N,N-dimethylformamide. The reaction may be performed in the presence of a suitable base, e.g. an inorganic base such as potassium carbonate.

Alternatively, the intermediates of formula (V), (VIII) and (IX) wherein Y represents —S— may be prepared by reacting a compound of formula (XIII) with a compound of formula (XIV):

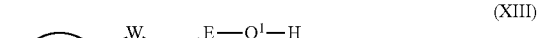

(XIII)

(XIV)

wherein M, W, E, $Q^1$, $R^a$ and $L^3$ are as defined above; under conditions analogous to those described above for the reaction between compounds (XI) and (XII).

The intermediates of formula (XIII) may be prepared from the corresponding intermediate of formula (XI) above by treatment with a thioacetate salt, e.g. an alkali metal thioacetate such as potassium thioacetate; followed by treatment of the resulting material with an acid, e.g. a mineral acid such as hydrochloric acid.

The intermediates of formula (XI) wherein E represents (methyl)methylene and $Q^1$ represents NH may be prepared by a three-step procedure which comprises: (i) treating a suitable compound of formula (XV):

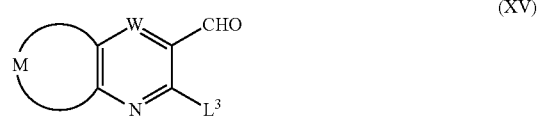

(XV)

wherein M, W and $L^3$ are as defined above; with 2-methyl-2-propanesulfinamide in the presence of titanium(IV) isopropoxide; (ii) reaction of the resulting compound with a Grignard reagent, e.g. methylmagnesium bromide; and (iii) treatment of the resulting compound with a mineral acid, e.g. hydrochloric acid.

Similarly, the intermediates of formula (XI) wherein E represents methylene and $Q^1$ represents NH may be prepared by a three-step procedure which comprises: (i) treating a suitable compound of formula (XV) above with 2-methyl-2-propanesulfinamide in the presence of titanium(IV) isopropoxide; (ii) reaction of the resulting compound with a reducing reagent, e.g. sodium borohydride; and (iii) treatment of the resulting compound with a mineral acid, e.g. hydrochloric acid.

Where they are not commercially available, the starting materials of formula (IV), (VI), (VII), (X), (XII), (XIV) and (XV) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art. By way of example, a compound of formula (I) wherein Z contains a halogen atom, e.g. chloro, may be converted into the corresponding compound of formula (I) wherein Z contains an amino (—$NH_2$) moiety by treatment with ammonia, typically in the presence of an ammonium salt, e.g. ammonium hydroxide.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, $3^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 μM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the $IC_{50}$ When tested in the above assay, the compounds of the accompanying Examples were all found to possess $IC_{50}$ values for inhibition of activity of human PI3Kα and/or PI3Kβ and/or PI3Kγ and/or PI3Kδ of 50 μM or better.

EXAMPLES

Abbreviations

DCM: dichloromethane
$Et_2O$: diethyl ether
DIPEA: N,N-diisopropylethylamine
EtOAc: ethyl acetate
MeOH: methanol
MeCN: acetonitrile
THF: tetrahydrofuran
TFA: trifluoroacetic acid
DMF: N,N-dimethylformamide
DMSO: dimethylsulfoxide
r.t.: room temperature
RT: retention time
$SiO_2$: silica
h: hour
br: broad
M: mass
HPLC: High Performance Liquid Chromatography
LCMS: Liquid Chromatography Mass Spectrometry
ES+: Electrospray Positive Ionisation
Analytical Conditions All NMRs were obtained at 400 MHz.

Compounds were named with the aid of the Cambridgesoft Chemistry Cartridge (v. 9.0.0.182) software.

All reactions involving air- or moisture-sensitive reagents were performed under a nitrogen atmosphere using dried solvents and glassware.

| Analytical Condition | Method | Description | |
|---|---|---|---|
| 10cm_ESCI_AmmBicarb_MeCN<br>10cm_ESCI_Bicarb_MeCN<br>10cm_ESI_Bicarb<br>10cm_ESI_Bicarb_MeCN<br>10cm_APCI_Formic | 1 | Solvents: | Acetonitrile (far UV grade) Water (high purity via PureLab Option unit) with 10 mM ammonium hydrogencarbonate |
| | | Column: | Waters Xterra MS 5 μm C18, 100 × 4.6 mm (Plus guard cartridge) |
| | | Flow Rate: | 2 mL/min |
| | | Gradient: | A: Water/Bicarb<br>B: MeCN |

| Time | A % | B % |
|---|---|---|
| 0.00 | 95 | 5 |
| 0.50 | 95 | 5 |
| 4.00 | 5 | 95 |
| 5.50 | 5 | 95 |
| 5.60 | 95 | 5 |
| 6.50 | 95 | 5 |

| | | | |
|---|---|---|---|
| 10cm_ESI_Formic<br>10cm_ESI_Formic_MeCN | 2 | Solvents: | Acetonitrile (far UV grade) with 0.1% (v/v) formic acid Water (high purity via PureLab Option unit) with 0.1% formic acid |
| | | Column: | Phenomenex Luna 5 μm C18 (2), 100 × 4.6 mm (Plus guard cartridge) |
| | | Flow Rate: | 2 mL/min |
| | | Gradient: | A: Water/formic acid<br>B: MeCN/formic acid |

| Time | A % | B % |
|---|---|---|
| 0.00 | 95 | 5 |
| 3.50 | 5 | 95 |
| 5.50 | 5 | 95 |
| 5.60 | 95 | 5 |
| 6.50 | 95 | 5 |

| | | | |
|---|---|---|---|
| 15cm_Formic_Ascentis_HPLC_CH3CN | 3 | Solvents: | Acetonitrile (far UV grade) with 0.1% (v/v) formic acid Water (high purity via |

-continued

| Analytical Condition | Method | Description |
|---|---|---|
| | Column: | PureLab Ultra unit) with 0.1% formic acid Supelco, Ascentis® Express C18, 2.7 µm C18, 150 × 4.6 mm |
| | Flow Rate: | 1 mL/min |
| | Gradient: | A: Water/formic acid B: MeCN/formic acid |

| Time | A % | B % |
|---|---|---|
| 0.00 | 96 | 4 |
| 3.00 | 96 | 4 |
| 9.00 | 0 | 100 |
| 13.6 | 0 | 100 |
| 13.7 | 96 | 4 |
| 15.0 | 96 | 4 |

Intermediate 1

(R,E)-N-[(2,8-Dichloroquinolin-3-yl)methylidene]-2-methylpropane-2-sulfinamide

To a solution of 2,8-dichloroquinoline-3-carboxaldehyde (43.0 g, 0.19 mol) in anhydrous THF (500 mL) was added titanium(IV) isopropoxide (114 mL, 0.38 mol) at r.t. After stirring for 15 minutes, (R)-2-methyl-2-propanesulfinamide (23.0 g, 0.19 mol) was added and stirring was continued for 17 h at r.t. Water (1 L) was added to the reaction mixture and the resulting precipitate was filtered and washed with DCM. The organic layer was dried ($Na_2SO_4$) and concentrated in vacuo to give the title compound (61 g, 97%) as a pale yellow solid. $\delta_H$ (CDCl$_3$) 9.11 (1H, s), 8.83 (1H, s), 7.93 (1H, dd, J7.54, 1.31 Hz), 7.88 (1H, dd, J 8.22, 1.31 Hz), 7.55 (1H, t, J 7.88 Hz), 1.33 (9H, s).

Intermediate 2

(R)—N—[(S)-1-(2,8-Dichloroquinolin-3-yl)ethyl]-2-methylpropane-2-sulfinamide

To a solution of Intermediate 1 (61 g, 0.18 mol) in DCM (1.5 L) was added dropwise methylmagnesium bromide (123.5 mL, 0.37 mol; 3M in Et$_2$O) over 50 minutes at −70° C. under nitrogen. The reaction mixture was allowed to reach r.t. with stirring overnight. The mixture was cooled in an ice-salt bath and saturated aqueous NH$_4$Cl (500 mL) was slowly added. The aqueous layer was extracted with DCM (2×500 mL). The combined organic layers were dried (MgSO$_4$) and concentrated in vacuo. The residue was triturated with Et$_2$O and the solid filtered, washed with Et$_2$O and dried under reduced pressure to give the title compound (32 g, 50%) as a pale pink solid. $\delta_H$ (CDCl$_3$) 8.26 (1H, s), 7.83 (1H, dd, J 7.52, 1.32 Hz), 7.74 (1H, dd, J 8.19, 1.32 Hz), 7.49 (1H, t, J 7.86 Hz), 5.16-5.07 (1H, m), 3.47 (1H, d, J 4.63 Hz), 1.71 (3H, d, J 6.75 Hz), 1.25 (9H, s).

Intermediate 3

(S)-1-(2,8-Dichloroquinolin-3-yl)ethanamine

To a solution of Intermediate 2 (37.7 g, 0.11 mol) in MeOH (370 mL) was added 4M hydrogen chloride in 1,4-dioxane (58 mL) at r.t. The reaction mixture was stirred for 2 h and concentrated in vacuo. The residue was partitioned between 5M HCl (300 mL) and DCM (300 mL). The organic layer was extracted with 5M aqueous HCl (100 mL) and the combined aqueous layers basified with aqueous NaOH and extracted with DCM (3×500 mL) and chloroform (3×500 mL). The organic layers were dried (MgSO$_4$) and concentrated in vacuo to afford the title compound (23.7 g, 90%) as an amber oil. $\delta_H$ (CDCl$_3$) 8.40 (1H, s), 7.80 (1H, dd, J 7.51, 1.33 Hz), 7.75 (1H, dd, J 8.19, 1.33 Hz), 7.46 (1H, t, J 7.86 Hz), 4.67 (1H, q, J 6.52 Hz), 1.50 (3H, d, J 6.53 Hz).

Intermediate 4

(S)-tert-Butyl 1-(2,8-dichloroquinolin-3-yl)ethylcarbamate

To a stirred solution of Intermediate 3 (23.7 g, 98 mmol) and DIPEA (51 mL, 0.3 mol) in DCM (1 L) was added di-tert-butyl dicarbonate (25.7 g, 118 mmol). The reaction mixture was allowed to stand at r.t. overnight and concentrated in vacuo. The residue was triturated with 40-60 petroleum ether, filtered, washed with 40-60 petroleum ether and dried under reduced pressure to give the title compound (28.4 g, 85%) as a colourless solid. $\delta_H$ (CDCl$_3$) 8.13 (1H, s), 7.80 (1H, dd, J 7.51, 1.32 Hz), 7.72 (1H, dd, J 8.18, 1.31 Hz), 7.46 (1H, t, J 7.85 Hz), 5.23-5.16 (1H, m), 5.10 (1H, br s), 1.55 (3H, br d, J 7.18 Hz), 1.42 (9H, br s).

Intermediate 5

(E)-N-[(2-Chloro-7-fluoro-8-methylquinolin-3-yl)methylidene]-(R)-2-methylpropane-2-sulfinamide Following the procedure described for Intermediate 1, 2-chloro-7-fluoro-8-methylquinoline-3-carbaldehyde (6.6 g, 29.5 mmol), titanium(IV) isopropoxide (17 g, 60 mmol) and (R)-(+)-2-methyl-2-propanesulfinamide (3.6 g, 29.5 mmol) afforded the title compound (8.3 g, 86%) as a yellow solid. $\delta_H$ (CDCl$_3$) 9.12 (1H, s), 8.73 (1H, s), 7.71 (1H, dd, J 6.0 Hz), 7.40 (1H, t, J 8.2 Hz), 2.69 (3H, s), 1.32 (9H, s).

Intermediate 6

N—[(S)-1-(2-Chloro-7-fluoro-8-methylquinolin-3-yl)ethyl]-(R)-2-methylpropane-2-sulfinamide Following the procedure described for Intermediate 2, Intermediate 5 (8.3 g, 25.4 mmol) and methylmagnesium bromide (16.0 mL, 48 mmol; 3.0M in Et$_2$O) afforded, after crystallisation from 40-60 petroleum ether, the title compound (4.2 g, 48%) as a yellow solid. $\delta_H$ (CDCl$_3$) 8.17 (1H, s), 7.63 (1H, dd, J 6.0 Hz), 7.32 (1H, t, J 8.8 Hz), 5.16 (1H, q, J 6.8 Hz), 3.45 (1H, d, J 6.8 Hz), 2.66 (3H, s) 1.70 (3H, d, J 6.8 Hz), 1.26 (9H, s).

Intermediate 7

(S)-tert-Butyl 1-(2-chloro-7-fluoro-8-methylquinolin-3-yl)ethylcarbamate

To a solution of Intermediate 6 (4.2 g, 12.2 mmol) in MeOH (20 mL) was added conc. HCl (1 mL) and the mixture was stirred at r.t. for 2 h. The reaction mixture was partitioned between DCM (100 mL) and 2M NaOH solution (50 mL). The organic layer was dried (MgSO$_4$) and filtered. To this filtrate was added DIPEA (1.6 g, 12.2 mmol), followed by a solution of di-tert-butyl dicarbonate (2.7 g, 12.2 mmol) in DCM (10 mL) dropwise. The reaction mixture was stirred at r.t. for 3 h, then diluted with DCM (10 mL) and washed with saturated NaHCO₃ solution (15 mL) and brine (15 mL). The organic layer was dried (MgSO₄), concentrated in vacuo and purified by column chromatography on silica, eluting with 0-30% EtOAc in 40-60 petroleum ether, to give the title compound (4.38 g, 100%) as a yellow solid. $\delta_H$ (CDCl₃) 8.07 (1H, s), 7.62 (1H, dd, J 6.0 Hz), 7.30 (1H, t, J 8.8 Hz), 5.17 (1H, m), 5.07 (1H, br s), 2.65 (3H, s), 1.54 (3H, d, J 6.4 Hz), 1.42 (9H, s).

Intermediate 8

(S)-tert-Butyl 1-[2-(2-amino-2-oxoethylthio)-7-fluoro-8-methylquinolin-3-yl]ethylcarbamate A suspension of Intermediate 7 (115.2 mg, 0.34 mmol), K₂CO₃ (47 mg, 0.34 mmol) and 2-mercaptoacetamide (0.46 mL, 0.509 mmol; 10% solution in methanolic ammonia) in DMF (1.5 mL) was heated at 120° C. under microwave irradiation for 1 h. After cooling, the mixture was dissolved in a 1:1 mixture of EtOAc and Et₂O (150 mL) and washed with saturated brine (3×30 mL). The organic layer was dried (MgSO₄) and concentrated in vacuo. Purification by column chromatography on silica, eluting with 50% EtOAc in DCM, afforded the title compound (96 mg, 72%) as a white solid. $\delta_H$ (DMSO-d₆) 8.14 (1H, s), 7.83 (1H, dd, J 8.94, 6.21 Hz), 7.70-7.58 (2H, m), 7.41 (1H, t, J 9.13 Hz), 7.18 (1H, s), 4.94 (1H, t, J 7.05 Hz), 4.10 (1H, d, J 14.93 Hz), 4.02 (1H, d, J 14.93 Hz), 2.62 (3H, d, J 2.26 Hz), 1.48-1.38 (12H, m).

Intermediate 9

(S)-tert-Butyl 1-[7-fluoro-2-(isopropylthio)-8-methylquinolin-3-yl]ethylcarbamate A suspension of Intermediate 7 (300 mg, 0.885 mmol), K₂CO₃ (122.4 mg, 0.885 mmol) and 2-propanethiol (0.185 mL, 1.99 mmol) in DMF (3 mL) was heated at 120° C. under microwave irradiation for 2 h. After cooling, the mixture was dissolved in a 1:1 mixture of EtOAc and Et₂O (400 mL) and washed with saturated brine (3×80 mL). The organic layer was dried (MgSO₄) and concentrated in vacuo. Purification by column chromatography on silica, eluting with 1% EtOAc in DCM, afforded the title compound (261 mg, 78%) as a white solid. $\delta_H$ (CDCl₃) 7.81 (1H, s), 7.52 (1H, dd, J 8.90, 6.05 Hz), 7.16 (1H, t, J 9.00 Hz), 5.08-4.85 (2H, m), 4.36-4.30 (1H, m), 2.64 (3H, d, J 2.37 Hz), 1.54-1.47 (9H, m), 1.41 (9H, br s).

Example 1

(S)-2-{8-Chloro-3-[1-(pyrrolo[2,1-f][1,2,4]triazin-4-ylamino)ethyl]quinolin-2-ylthio}acetamide A suspension of Intermediate 4 (116 mg, 0.339 mmol), K₂CO₃ (46.9 mg, 0.339 mmol), 2-mercaptoacetamide (0.463 mL, 0.509 mmol; 10% solution in methanolic ammonia) in DMF (1.5 mL) was heated to 110° C. under microwave irradiation for 1 h. After cooling, the mixture was dissolved in a 1:1 mixture of EtOAc and Et₂O (150 mL) and washed with saturated brine (3×30 mL). The organic layer was dried (MgSO₄) and concentrated in vacuo to give a yellow solid (136 mg). LCMS (ES+) 396 (M+H)⁺. The yellow solid was dissolved in DCM (20 mL), treated with TFA (2 mL), stirred at room temperature for 2 h and concentrated in vacuo. The yellow residue was basified with 0.2M NaOH (10 mL) and extracted with EtOAc (3×15 mL). The combined organic layers were dried (MgSO₄) and concentrated in vacuo to give a yellow foam (136 mg). LCMS (ES+) 296 (M+H)⁺. A solution of this foam (67.1 mg, 0.227 mmol), 4-bromo-pyrrolo[2,1-f][1,2,4]triazine (67.4 mg, 0.340 mmol) and DIPEA (0.118 mL, 0.68 mmol) in isopropanol (1.5 mL) was stirred at room temperature overnight and evaporated. The residue was partitioned between EtOAc (70 mL) and saturated brine (15 mL). The aqueous layer was extracted with EtOAc (50 mL) and the combined organic layer dried (MgSO₄) and concentrated in vacuo. Purification by preparative HPLC afforded the title compound (24.3 mg, 26%) as a white solid. $\delta_H$ (DMSO-d₆) 8.65 (1H, d, J 7.0 Hz), 8.33 (1H, s), 7.97 (1H, dd, J 8.1, 1.3 Hz), 7.91 (1H, dd, J 7.6, 1.3 Hz), 7.88 (1H, s), 7.67 (1H, dd, J 2.6, 1.6 Hz), 7.61 (1H, s), 7.51 (1H, t, J 7.8 Hz), 7.24 (1H, s), 7.07 (1H, dd, J 4.4, 1.6 Hz), 6.68 (1H, dd, J 4.4, 2.6 Hz), 5.73 (1H, t, J 6.9 Hz), 4.20 (1H, d, J 14.9 Hz), 4.06 (1H, d, J 14.9 Hz), 1.72 (3H, d, J 6.8 Hz). LCMS (ES+) 413 (M+H)⁺, RT 3.04 minutes (Method 2).

Example 2

(S)-2-{3-[1-(4-Amino-6-methyl-[1,3,5]triazin-2-ylamino)ethyl]-8-chloroquinolin-2-ylthio}acetamide A suspension of Intermediate 4 (116 mg, 0.339 mmol), K₂CO₃ (46.9 mg, 0.339 mmol), 2-mercaptoacetamide (0.463 mL, 0.509 mmol; 10% solution in methanolic ammonia) in DMF (1.5 mL) was heated to 110° C. under microwave irradiation for 1 h. After cooling, the mixture was dissolved in EtOAc and Et₂O (1:1, 150 mL) and washed with saturated brine (3×30 mL). The organic layer was dried (MgSO₄) and concentrated in vacuo to give a yellow solid (136 mg). LCMS (ES+) 396 (M+H)⁺. The yellow solid was dissolved in DCM (20 mL) and TFA (2 mL) was added. The mixture was stirred at room temperature for 2 h and evaporated. The yellow residue obtained was basified with 0.2M NaOH (10 mL) and extracted with EtOAc (3×15 mL). The combined organic layers were dried (MgSO₄) and concentrated in vacuo to give a yellow foam (136 mg). LCMS (ES+) 296 (M+H)⁺. A solution of this foam (69.2 mg, 0.234 mmol), 2-amino-4-chloro-6-methyl-[1,3,5]triazine (40.6 mg, 0.281 mmol) and DIPEA (0.122 mL, 0.702 mmol) in isopropanol (1.5 mL) was heated to 140° C. under microwave irradiation for 1 h. The solvent was removed in vacuo and the residue was partitioned between EtOAc (70 mL) and saturated brine (15 mL). The aqueous layer was extracted with EtOAc (50 mL) and the combined organic layers were dried (MgSO₄) and concentrated in vacuo. Purification by column chromatography on silica, eluting with DCM/MeOH/NH₃ solution (95:4:1), afforded the title compound (33.6 mg, 36%) as a white solid. $\delta_H$ (DMSO-d₆) 8.26 (1H, s), 7.94-7.85 (3H, m), 7.63 (1H, s), 7.50 (1H, t, J 7.8 Hz), 7.24 (1H, s), 6.66-6.53 (2H, m), 5.37 (1H, s), 4.14 (2H, m), 2.09 (3H, m), 1.54 (3H, d, J 6.8 Hz). LCMS (ES+) 404 (M+H)⁺, RT 7.30 minutes (Method 3).

Example 3

2-({7-Fluoro-8-methyl-3-[(1S)-1-(9H-purin-6-ylamino)ethyl]quinolin-2-yl}sulfanyl)-acetamide To a solution of Intermediate 8 (95 mg, 0.241 mmol) in DCM (14 mL) was added TFA (1.4 mL). The reaction mixture was stirred at r.t. for 2 h. The excess solvent was removed in vacuo. The residue was basified with 0.2M aqueous NaOH (10 mL) and extracted with EtOAc (3×20 mL). The combined organic layers were dried (MgSO₄) and concentrated in vacuo to give a yellow solid (77 mg, 100%). LCMS (ES+) 294 (M+H)⁺. A solution of this solid (76 mg, 0.193 mmol), 6-chloropurine (74.6 mg, 0.483 mmol) and DIPEA (0.135 mL, 0.772 mmol) in n-butanol (2 mL) was heated at 120° C. under microwave irradiation for 2 h. The excess solvent was concentrated in vacuo and the residue obtained was suspended in a mixture of water (5 mL) and DCM (20 mL). The mixture was eluted through an IST phase separator cartridge (washed thoroughly with DCM) and the filtrate was concentrated in vacuo. Purification by preparative HPLC afforded the title compound (41.7 mg, 52%) as an off-white solid. $\delta_H$ (DMSO-d$_6$) 13.00 (1H, br s), 8.27 (2H, s), 8.21-8.15 (2H, m), 7.82-7.75 (1H, m), 7.61 (1H, s), 7.38 (1H, t, J 9.11 Hz), 7.21 (1H, s), 5.85-5.70 (1H, m), 4.12 (1H, d, J 15.35 Hz), 4.03 (1H, d, J 15.30 Hz), 2.62 (3H, s), 1.69 (3H, d, J 6.81 Hz). LCMS (ES+) 412 (M+H)$^+$, RT 2.28 minutes (Method 2).

Example 4

2-({7-Fluoro-8-methyl-3-[(1S)-1-(9H-purin-6-ylamino)ethyl]quinolin-2-yl}sulfanyl)-ethanol A suspension of Intermediate 7 (71.3 mg, 0.21 mmol), K$_2$CO$_3$ (29.1 mg, 0.21 mmol) and 2-mercaptoethanol (24.7 mg, 0.316 mmol) in DMF (1 mL) was heated at 120° C. under microwave irradiation for 1 h. After cooling, the mixture was dissolved in a 1:1 mixture of EtOAc and Et$_2$O (100 mL) and washed with saturated brine (3×20 mL). The organic layer was dried (MgSO$_4$) and concentrated in vacuo. Purification by column chromatography on silica, eluting with 10% EtOAc in DCM, gave a white solid (51 mg, 64%). LCMS (ES+) 381 (M+H)$^+$. This solid (51 mg, 0.134 mmol) was dissolved in DCM (3.5 mL) and TFA (0.62 mL) was added. The reaction mixture was stirred at r.t. for 1.5 h and concentrated in vacuo. The residue obtained was basified with 0.4M aqueous NaOH (10 mL) and extracted with EtOAc (3×20 mL). The combined organic layers were dried (MgSO$_4$) and concentrated in vacuo. Purification by column chromatography on silica, eluting with DCM/MeOH/NH$_3$ solution in MeOH (97:2:1), gave a white solid (33 mg, 88%). LCMS (ES+) 281 (M+H)$^+$. A solution of this solid (28.2 mg, 0.101 mmol), 6-chloropurine (23.3 mg, 0.151 mmol) and DIPEA (0.053 mL, 0.302 mmol) in n-butanol (1 mL) was heated at 130° C. under microwave irradiation for 1 h. Purification by preparative HPLC afforded the title compound (13.6 mg, 34%) as a yellow solid. $\delta_H$ (DMSO-d$_6$) 8.24 (2H, 2 s), 8.18 (2H, d, J 6.73 Hz), 7.77 (1H, t, J 7.52 Hz), 7.37 (1H, t, J 9.13 Hz), 5.82-5.65 (1H, m), 5.12-4.97 (1H, m), 3.81 (2H, t, J 6.67 Hz), 3.61-3.54 (2H, m), 3.50-3.45 (1H, m), 2.63 (3H, d, J 2.18 Hz), 1.66 (3H, d, J 6.85 Hz). LCMS (ES+) 399 (M+H)$^+$, RT 2.45 minutes (Method 2).

Example 5

3-({7-Fluoro-8-methyl-3-[(1S)-1-(9H-purin-6-ylamino)ethyl]quinolin-2-yl}sulfanyl)-propane-1,2-diol A suspension of Intermediate 7 (115.2 mg, 0.34 mmol), K$_2$CO$_3$ (47 mg, 0.34 mmol) and 3-mercapto-1,2-propanediol (55.2 mg, 0.51 mmol) in DMF (1.5 mL) was heated at 120° C. under microwave irradiation for 1 h. After cooling, the mixture was dissolved in a 1:1 mixture of EtOAc and Et$_2$O (150 mL) and washed with saturated brine (3×30 mL). The organic layer was dried (MgSO$_4$) and concentrated in vacuo. Purification by column chromatography on silica, eluting with 50% EtOAc in DCM, gave a white solid (92 mg, 64%). LCMS (ES+) 411 (M+H)$^+$ (mixture of diastereoisomers). This solid (92 mg, 0.224 mmol) was dissolved in DCM (13 mL) and TFA (1.3 mL) was added. The reaction mixture was stirred at r.t. for 1.5 h and concentrated in vacuo. The residue obtained was basified with 0.4M aqueous NaOH (10 mL) and extracted with EtOAc (3×20 mL). The combined organic layers were dried (MgSO$_4$) and concentrated in vacuo. Purification by column chromatography on silica, eluting with DCM/MeOH/NH$_3$ solution in MeOH (97:2:1), gave a colourless glass (49 mg, 70%). LCMS (ES+) 311 (M+H)$^+$ (mixture of diastereoisomers). A solution of this material (49 mg, 0.158 mmol), 6-chloropurine (36.6 mg, 0.237 mmol) and DIPEA (0.083 mL, 0.474 mmol) in n-butanol (1 mL) was heated at 130° C. under microwave irradiation for 1 h. Purification by preparative HPLC afforded the title compound (4.2 mg, 6%) (only one of the diastereoisomers) as an off-white solid. $\delta_H$ (DMSO-d$_6$) 8.24 (2H, 2 s), 8.21-8.16 (2H, m), 7.80-7.73 (1H, m), 7.37 (1H, t, J 9.35 Hz), 5.83-5.67 (1H, m), 5.06 (1H, br s), 4.73 (1H, m), 3.87 (1H, br s), 3.69 (1H, d, J 13.66 Hz), 3.52 (3H, s), 3.36 (1H, masked by H$_2$O), 2.63 (3H, s), 1.66 (3H, d, J 6.55 Hz). LCMS (ES+) 429 (M+H)$^+$, RT 2.30 minutes (Method 2).

Example 6

N-{(1S)-1-[7-Fluoro-8-methyl-2-(propan-2-ylsulfanyl)quinolin-3-yl]ethyl}pyrrolo[2,1-f]-[1,2,4]triazin-4-amine To a solution of Intermediate 9 (126 mg, 0.333 mmol) in DCM (8.7 mL) was added TFA (1.52 mL). The mixture was stirred at r.t. for 1.5 h. The excess solvent was concentrated in vacuo. The residue obtained was basified with 0.7M aqueous NaOH (10 mL) and extracted with EtOAc (3×35 mL). The combined organic layers were dried (MgSO$_4$) and concentrated in vacuo to give a pale yellow gum (106 mg, 100%). LCMS (ES+) 279 (M+H)$^+$. A solution of this material (53 mg, 0.19 mmol), 4-bromopyrrolo[2,1-f][1,2,4]triazine (56.6 mg, 0.286 mmol) and DIPEA (0.1 mL, 0.57 mmol) in n-butanol (1 mL) was heated at 130° C. under microwave irradiation for 1 h. Purification by preparative HPLC afforded the title compound (29.2 mg, 39%) as a cream solid. $\delta_H$ (DMSO-d$_6$) 8.59 (1H, d, J 7.14 Hz), 8.21 (1H, s), 7.87-7.81 (2H, m), 7.66 (1H, dd, J 2.61, 1.56 Hz), 7.39 (1H, t, J 9.15 Hz), 7.09 (1H, d, J 4.31 Hz), 6.68 (1H, dd, J 4.36, 2.61 Hz), 5.64 (1H, t, J 6.93 Hz), 4.34-4.26 (1H, m), 2.63 (3H, d, J 2.23 Hz), 1.66 (3H, d, J 6.85 Hz), 1.53 (6H, 2 d, J 6.80 Hz). LCMS (ES+) 396 (M+H)$^+$, RT 4.49 minutes (Method 1).

Example 7

N-{(1S)-1-[7-Fluoro-8-methyl-2-(propan-2-ylsulfanyl)quinolin-3-yl]ethyl}-9H-purin-6-amine To a solution of Intermediate 9 (126 mg, 0.333 mmol) in DCM (8.7 mL) was added TFA (1.52 mL). The mixture was stirred at r.t. for 1.5 h. The excess solvent was concentrated in vacuo. The residue was basified with 0.7M aqueous NaOH (10 mL) and extracted with EtOAc (3×35 mL). The combined organic layers were dried (MgSO$_4$) and concentrated in vacuo to give a pale yellow gum (106 mg, 100%). LCMS (ES+) 279 (M+H)$^+$. A solution of this material (53 mg, 0.19 mmol), 6-chloropurine (44.1 mg, 0.286 mmol) and DIPEA (0.1 mL, 0.571 mmol) in n-butanol (1 mL) was heated at 130° C. under microwave irradiation for 1 h. Purification by preparative HPLC afforded the title compound (20.2 mg, 27%) as a yellow solid. $\delta_H$ (DMSO-d$_6$) 12.99 (1H, br s), 8.30-8.17 (2H, m), 8.17 (2H, br s), 7.80-7.72 (1H, m), 7.36 (1H, t, J 9.03 Hz), 5.75-5.62 (1H, m), 4.35-4.26 (1H, m), 2.63 (3H, s), 1.63 (3H, d, J 6.80 Hz), 1.53 (6H, d, J 6.79 Hz). LCMS (ES+) 397 (M+H)+, RT 3.46 minutes (Method 1).

Example 8

2-[(3-{(1S)-1-[(2-Amino-5-cyanopyrimidin-4-yl) amino]ethyl}-7-fluoro-8-methyl-quinolin-2-yl)sulfanyl]-N-methylacetamide A suspension of Intermediate 7 (500 mg, 1.48 mmol), $K_2CO_3$ (204 mg, 1.48 mmol) and potassium thioacetate (590 mg, 5.16 mmol) in DMF (5.5 mL) was heated at 140° C. under microwave irradiation for 3 h. After cooling, the mixture was dissolved in water (20 mL), neutralized to pH 6 with 1M HCl and extracted with EtOAc (3×50 mL). The organic layer was washed with saturated brine (3×30 mL), dried ($MgSO_4$) and concentrated in vacuo. Purification by column chromatography on silica, eluting with 5% EtOAc in DCM, gave a yellow solid (127 mg, 26%). LCMS (ES+) 337 (M+H)+. A suspension of this solid (114 mg, 0.339 mmol), $K_2CO_3$ (46.8 mg, 0.339 mmol) and 2-chloro-N-methylacetamide (87 mg, 0.809 mmol) in DMF (3 mL) was heated at 120° C. under microwave irradiation for 1 h. After cooling, the mixture was dissolved in a 1:1 mixture of EtOAc and $Et_2O$ (150 mL) and washed with saturated brine (3×30 mL). The organic layer was dried ($MgSO_4$) and concentrated in vacuo. Purification by column chromatography on silica, eluting with 40% EtOAc in DCM, gave a white solid (119 mg, 86%). LCMS (ES+) 408 (M+H)+. This solid (119 mg, 0.292 mmol) was dissolved in DCM (7.6 mL) and TFA (1.33 mL) was added. The reaction mixture was stirred at r.t. for 1.5 h and concentrated in vacuo. The residue obtained was basified with 0.8M aqueous NaOH (8 mL) and extracted with EtOAc (3×30 mL). The combined organic layers were dried ($MgSO_4$) and concentrated in vacuo to give a colourless glass (117 mg, 100%). LCMS (ES+) 308 (M+H)+. A solution of this material (117 mg, 0.292 mmol), 2,4-dichloro-5-cyanopyrimidine (76.2 mg, 0.438 mmol) and DIPEA (0.20 mL, 1.168 mmol) in THF (2 mL) was stirred at r.t. for 4 h. The mixture was dissolved in EtOAc (150 mL) and washed with saturated brine (3×30 mL). The organic layer was dried ($MgSO_4$) and concentrated in vacuo. Purification by column chromatography on silica, eluting with DCM/MeOH/$NH_3$ solution in MeOH (98:1:1), gave a pale brown foam (105 mg, 81%). LCMS (ES+) 445, 447 (M+H)+ (mixture of regioisomers). A solution of this material (105 mg, 0.236 mmol) in a mixture of 7M $NH_3$ solution in MeOH (2 mL) and $NH_4OH$ (1 mL) was heated at 120° C. under microwave irradiation for 1 h. After cooling, the mixture was dissolved in saturated brine (40 mL) and extracted with EtOAc (3×100 mL). The organic layer was dried ($MgSO_4$) and concentrated in vacuo. Purification by preparative HPLC afforded the title compound (13.2 mg, 13%) as an off-white solid. $\delta_H$ (DMSO-$d_6$) 8.31 (1H, s), 8.25 (1H, s), 8.15 (1H, d, J 5.33 Hz), 7.87-7.81 (2H, m), 7.40 (1H, t, J 9.13 Hz), 7.15 (1H, br s), 6.97 (1H, br s), 5.55-5.46 (1H, m), 4.10 (1H, d, J 15.2 Hz), 4.04 (1H, d, J 15.2 Hz), 2.65 (3H, d, J 4.59 Hz), 2.58 (3H, s), 1.61 (3H, d, J 6.82 Hz). LCMS (ES+) 426 (M+H)+, RT 3.37 minutes (Method 1).

Example 9

2-[(3-{(1S)-1-[(4-Amino-5-cyanopyrimidin-2-yl) amino]ethyl}-7-fluoro-8-methyl-quinolin-2-yl)sulfanyl]-N-methylacetamide Obtained as an additional product from Example 8, which afforded the title compound (10.4 mg, 10%) as a white solid. $\delta_H$ (DMSO-$d_6$) (mixture of rotamers) 8.13-7.90 (4H, m), 7.71 (1H, dd, J 8.94, 6.30 Hz), 7.29 (1H, t, J 9.13 Hz), 7.07 (2H, br s), 5.32 (0.5H, br s), 5.22 (0.5H, br s), 4.04-3.88 (2H, m), 2.56 (3H, d, J 4.60 Hz), 2.48 (3H, s), 1.45 (3H, d, J 6.85 Hz). LCMS (ES+) 426 (M+H)+, RT 2.95 minutes (Method 2).

The invention claimed is:

1. A compound of formula (I) or an N-oxide thereof, or a pharmaceutically acceptable salt or solvate thereof:

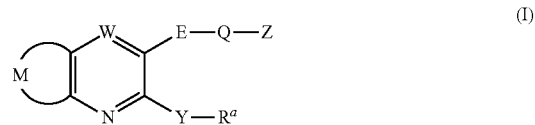

wherein
M represents the residue of an optionally substituted phenyl ring;
W represents C—$R^1$;
E represents an optionally substituted straight or branched $C_{1-4}$ alkylene chain;
Q represents N—$R^2$;
Z represents an optionally substituted mono- or bicyclic heteroaryl group containing at least one nitrogen atom selected from pyrrolyl, pyridinyl, indolyl, quinolinyl, isoquinolinyl, imidazolyl, pyrazolyl, triazolyl, pyridazinyl, pyrimidinyl, pyrazinyl, triazinyl, indazolyl, benzimidazolyl, furopyridinyl, thienopyridinyl, benzoxazolyl, benzothiazolyl, cinnolinyl, phthalazinyl, quinazolinyl, quinoxalinyl, imidazopyridinyl, pyrazolopyridinyl, purinyl, pyrazolopyrimidinyl, pyrrolopyrimidinyl, triazolopyrimidinyl, pyridopyrimidinyl, pyridopyrazinyl, pyridopyridazinyl, naphthyridinyl, pteridinyl, pyrrolotriazinyl and pyrazolotriazinyl;
Y represents —S—;
$R^1$ represents hydrogen, halogen, $C_{1-6}$ alkyl or $C_{1-6}$ alkoxy;
$R^2$ represents hydrogen or $C_{1-6}$ alkyl; and
$R^a$ represents trifluoromethyl; or $C_{1-6}$ alkyl, $C_{2-6}$ alkenyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl-($C_{1-6}$)alkyl, heteroaryl or heteroaryl($C_{1-6}$) alkyl, any of which groups may be optionally substituted by one or more substituents.

2. A compound as claimed in claim 1 represented by formula (IIA) or an N-oxide thereof, or a pharmaceutically acceptable salt or solvate thereof:

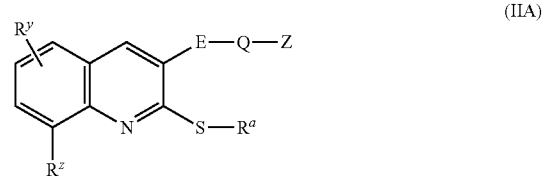

wherein E, Q, Z and $R^a$ are as defined in claim 1; and
$R^y$ and $R^z$ independently represent hydrogen, $C_{1-6}$ alkyl, $C_{3-7}$ cycloalkyl, $C_{3-7}$ cycloalkyl($C_{1-6}$)alkyl, aryl, aryl ($C_{1-6}$)alkyl, $C_{3-7}$ heterocycloalkyl, $C_{3-7}$ heterocycloalkyl($C_{1-6}$)alkyl, heteroaryl, heteroaryl($C_{1-6}$) alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$)alkylamino, halogen, cyano or trifluoromethyl.

3. A compound as claimed in claim 2 wherein $R^y$ represents hydrogen or halogen.

4. A compound as claimed in claim 2 wherein $R^z$ represents hydrogen, $C_{1-6}$ alkyl or halogen.

5. A compound as claimed in claim 1 wherein E represents methylene or (methyl)methylene.

6. A compound as claimed in claim 1 wherein Z represents pyrimidinyl, triazinyl, purinyl or pyrrolotriazinyl, any of which groups may be optionally substituted by one or more substituents independently selected from cyano, $C_{1-6}$ alkyl and amino.

7. A compound as claimed in claim 1 wherein $R^a$ represents $C_{1-6}$ alkyl, which group may be optionally substituted by one or more substituents independently selected from hydroxy, aminocarbonyl and ($C_{1-6}$)alkylamino-carbonyl.

8. A compound selected from the group consisting of
- (S)-2-{8-chloro-3-[1-(pyrrolo[2,1-f][1,2,4]triazin-4-ylamino)ethyl]quinolin-2-ylthio}acetamide;
- (S)-2-{3-[1-(4-amino-6-methyl-[1,3,5]triazin-2-ylamino)ethyl]-8-chloroquinolin-2-ylthio}acetamide;
- 2-({7-fluoro-8-methyl-3-[(1S)-1-(9H-purin-6-ylamino)ethyl]quinolin-2-yl}sulfanyl)-acetamide;
- 2-({7-fluoro-8-methyl-3-[(1S)-1-(9H-purin-6-ylamino)ethyl]quinolin-2-yl}sulfanyl)-ethanol;
- 3-({7-fluoro-8-methyl-3-[(1S)-1-(9H-purin-6-ylamino)ethyl]quinolin-2-yl}sulfanyl)-propane-1,2-diol;
- N-{(1S)-1-[7-fluoro-8-methyl-2-(propan-2-ylsulfanyl)quinolin-3-yl]ethyl}pyrrolo[2,1-f]-[1,2,4]triazin-4-amine;
- N-{(1S)-1-[7-fluoro-8-methyl-2-(propan-2-ylsulfanyl)quinolin-3-yl]ethyl}-9H-purin-6-amine;
- 2-[(3-{(1S)-1-[(2-amino-5-cyanopyrimidin-4-yl)amino]ethyl}-7-fluoro-8-methyl-quinolin-2-yl)sulfanyl]-N-methylacetamide;
- 2-[(3-{(1S)-1-[(4-amino-5-cyanopyrimidin-2-yl)amino]ethyl}-7-fluoro-8-methyl-quinolin-2-yl)sulfanyl]-N-methylacetamide;

and a pharmaceutically acceptable salt, solvate, or N-oxide of any of the foregoing.

9. A pharmaceutical composition comprising a compound of formula (I) as defined in claim 1 or an N-oxide thereof, or a pharmaceutically acceptable salt or solvate thereof, in association with a pharmaceutically acceptable carrier.

* * * * *